United States Patent
Zhang et al.

(10) Patent No.: US 9,944,648 B2
(45) Date of Patent: Apr. 17, 2018

(54) ORGANIC COMPOUNDS

(71) Applicant: Intra-Cellular Therapies, Inc., New York, NY (US)

(72) Inventors: Qiang Zhang, Somerset, NJ (US); Youyi Peng, New York, NY (US); Peng Li, New Milford, NJ (US); J. David Beard, New York, NY (US); Lawrence P. Wennogle, Hillsborough, NJ (US); John Tomesch, Succasunna, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/110,613

(22) PCT Filed: Jan. 9, 2015

(86) PCT No.: PCT/US2015/010901
§ 371 (c)(1),
(2) Date: Jul. 8, 2016

(87) PCT Pub. No.: WO2015/106158
PCT Pub. Date: Jul. 16, 2015

(65) Prior Publication Data
US 2016/0326179 A1    Nov. 10, 2016
US 2017/0190703 A9    Jul. 6, 2017

Related U.S. Application Data

(60) Provisional application No. 61/925,608, filed on Jan. 9, 2014.

(51) Int. Cl.
C07D 487/04 (2006.01)
C07D 235/30 (2006.01)
C07D 277/82 (2006.01)
C07B 59/00 (2006.01)
C07D 401/12 (2006.01)

(52) U.S. Cl.
CPC .......... C07D 487/04 (2013.01); C07B 59/002 (2013.01); C07D 235/30 (2013.01); C07D 277/82 (2013.01); C07D 401/12 (2013.01); C07B 2200/05 (2013.01)

(58) Field of Classification Search
CPC .................................................. C07D 487/04
See application file for complete search history.

(56) References Cited

U.S. PATENT DOCUMENTS

| | | |
|---|---|---|
| 4,376,110 A | 3/1983 | David et al. |
| 4,946,778 A | 8/1990 | Ladner et al. |
| 5,530,101 A | 6/1996 | Queen et al. |
| 5,545,580 A | 8/1996 | Sheng et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,789,650 A | 8/1998 | Lonberg et al. |
| 5,880,141 A | 3/1999 | Tang et al. |
| 5,910,771 A | 6/1999 | Stumberg et al. |
| 5,932,448 A | 8/1999 | Tso et al. |
| 6,060,296 A | 5/2000 | Hoekstra et al. |
| 6,288,089 B1 | 9/2001 | Zawada et al. |
| 6,465,493 B1 | 10/2002 | Burgess et al. |
| 6,555,328 B1 | 4/2003 | Keesler et al. |
| 6,800,283 B2 | 10/2004 | Gong et al. |
| 7,129,073 B2 | 10/2006 | Liu et al. |
| 7,320,785 B2 | 1/2008 | Greengard et al. |
| 9,532,980 B2 | 1/2017 | Flajolet et al. |
| 2003/0100514 A1 | 5/2003 | Ahotupa et al. |
| 2004/0209878 A1 | 10/2004 | Guzi et al. |
| 2010/0143361 A1 | 6/2010 | Flajolet et al. |
| 2012/0114739 A1 | 5/2012 | Deng et al. |
| 2012/0225888 A1* | 9/2012 | Pendri .................. C07D 487/04 514/252.16 |

FOREIGN PATENT DOCUMENTS

| | | |
|---|---|---|
| WO | WO 1999/032619 | 7/1999 |
| WO | WO 2001/041768 | 6/2001 |
| WO | WO 2003/014321 | 2/2003 |
| WO | WO 2005/001114 | 1/2005 |
| WO | WO 2005/105987 | 11/2005 |
| WO | WO 2008/066626 | 6/2008 |
| WO | WO 2010/070238 A1 | 6/2010 |
| WO | WO 2015/106158 A1 | 7/2015 |

OTHER PUBLICATIONS

Chemical Abstracts Registry No. 349537-00-4, indexed in the Registry file on STN CAS Online on Jul. 31, 2001.*
Golub et al., Science, vol. 286, Oct. 15, 1999, pp. 531-537.*
Demange et al., "Synthesis and evaluation of new potent inhibitors of CK1 and CDk5, two kinases involved in Alzheimer's disease," Med Chem Res, 2013, 22:3247-3258.
Duan et al., "mTOR Generates and Auto-Amplification Loop by Triggering the βTrCP- and CK1α-Dependent Degradation of DEPTOR," Molecular Cell, 2011. 44:317-324.
English Language Abstract of EP2385946, Sanofi SA, Nov. 16, 2011, Espacenet, obtained via the Internet, date obtained: Jun. 16, 2017, 1 page, URL: <https://worldwide.espacenet.com/publicationDetails/biblio?CC=EP&NR=2385946A1&KC=A1&FT=D&ND=&date=20111116&DB=&locale=en_EP#>.
Pubchem, Compound Summary for CID 4782689, National Center for Biotechnology Information, (Retrieved Online), Date Accessed: Jul. 8, 2016, <URL:http://pubchem.ncbi.nlm.nih.gov/compound/4782689?from=summary%3E#section=Top>.
International Search Report for International Application No. PCT/US2015/010901, created by the International Search Authority, dated Jun. 9, 2015.

(Continued)

*Primary Examiner* — Laura L Stockton
(74) *Attorney, Agent, or Firm* — Hoxie & Associates LLC

(57) ABSTRACT

The invention provides novel compounds, composition comprising said compounds and methods for inhibiting CK1 as well as methods of treating CK1 related disorders such as Alzheimer's disease comprising administering a therapeutically effective amount of a CK1 inhibitor to a patient in need thereof.

8 Claims, No Drawings

(56) References Cited

OTHER PUBLICATIONS

Ebisawa et al., "Circadian Rhythms in the CNS and Peripheral Clock Disorders: Human Sleep Disorders and Clock Genes", Journal of Pharmacological Sciences, 2007, 103(2):150-154.
Flajolet et al., "Regulation of Alzheimer's disease amyloid-beta formation by casein kinase I", Proc. Natl. Acad. Sci. U.S.A., 2007, 104(10):4159-64.
Hanger et al., "Novel Phosphorylation Sites in Tau from Alzheimer Brain Support a Role for Casein Kinase 1 in Disease Pathogenesis", The Journal of Biological Chemistry, 2007, 282(32):23645-23654.
Yasojima et al., "Casein kinase 1 delta mRNA is upregulated in Alzheimer disease brain", Brain Research, 2000, 865:116-120.
Agostinis, P. et al., "A synthetic peptide substrate specific for casein kinase-1," FEBS Lett., 1989, 259(1), pp. 75-78.
Ahmed, K., "Significance of the Casein Kinase System in Cell Growth and Proliferation with Emphasis on Studies of the Androgenic Regulation of the Prostate," Cell Mol Biol., 1994, Res 40, pp. 1-11.
Amit, S. et al., "Axin-mediated CKI phosphorylation of β-catenin at Ser 45: a molecular switch for the Wnt pathway," Genes Dev., 2002, 16, pp. 1066-1076.
Behrend et al., "IC261, a specific inhibitor of the protein kinases casein kinase 1-delta and -epsilon, triggers the mitotic checkpoint and induces p53-dependent postmitotic effects," Oncogene 19, 2000, pp. 5303-5313.
Bird, "Single-Chain Antigen-Binding Proteins," Science, 1988, 242, pp. 423-426.
Chijiwa et al., "A Newly Synthesized Selectice Casein Kinase I Inhibitor, N-(2-Aminoethyl)-5-chloroisoquinoline-8-sulfonamide, and Affinity Purification of Casein Kinase I from Bovine Testis", J. Biol. Chem., 1989, 264, pp. 4924-4927.
Cote et al., "Generation of human monoclonal antibodies reactive with cellular antigen," Proc. Natl. Acad. Sci USA, 1983, 80, pp. 2026-2030.
Cong, F. et al., "Casein Kinase Iε Modulates the Signaling Specificities of Dishevelled," Mol Cell Biol., 2004, 24(5), pp. 2000-2011.
Cotten et al., "Ribozyme mediated destruction of RNA in vivo," Embo J., 1989, 8(12) pp. 3861-3866.
Davidson, G. et al., "Casein kinase 1γ couples Wnt receptor activation to cytoplasmic signal transduction," Nature, 2005, 438, pp. 867-872.
Desdouits, F. et al., "Dopamine- and cAMP-regulated phosphoprotein DARP-32: Phosphorylation of Ser-137 by casein kinas I inhibits dephosphorylation of Thr-34 by calcineurin," Proc Natl Acad Sci USA, 1995, 92, pp. 2682-2685.
Desjardins, PR et al., "Purification and Properties of Rat Liver Nuclear Protein Kinases,", Canadian Journal of Biochemistry, 1972, 50(12), pp. 1249-1259.
Fish et al., "Isolation and Characterization of Human Casein Kinase Iε(CKI), a Novel Member of the CKI Gene Family*," J. Biol. Chem. 1995, 270(25), pp. 14875-14883.
Ghoshal, N. et al., "A New Molecular Link between the Fibrillar and Granulovacuolar Lesions of Alzheimer's Disease", American Journal of Pathology, 1999, vol. 155, No. 4, pp. 1163-1172.
Gibson, "Antisense approaches to the gene therapy of cancer—'Recnac'[1],"Cancer and Metastasis Reviews, 1996 (15) pp. 287-299.
Godl, K. et al., "An efficient proteomics method to identify the cellular targets of protein kinase inhibitors," PNAS USA, 2003, 100(26), pp. 15434-15439.
Gompel, M. et al., "Meridianins, a new family of protein kinase inhibitors isolated from the Ascidian Aplidium meridianum," Bioorg Med Chem Lett., 2004, 14(7), pp. 1703-1707.
Good et al., "Expression of small, therapeutic RNAs in human cell Nuclei," Gene Therapy, 1997, pp. 45-54.
Grassi & Marini, "Ribozymes: Structure, Function and Potential Therapy for Dominant Genetic Disorders," Annals of Medicine, 1996, 28, pp. 499-510.
Gross, S.D. et al., "A Phosphatidylinositol 4,5-bisphosphate-sensitive Casein Kinase Iα Associates with Synaptic Vesicles and Phosphorylates a Subset of Vesicle Proteins," J. Cell Biol., 1995, 130, pp. 711-724.
Gross, S.D., et al., "Casein Kinase I: Spatial Organization and Positioning of a Multifunctional Protein Kinase Family," Cell Signal, 1998, 10, pp. 699-711.
Huse et al., "Generation of a Large Combinatorial Library of the Immunoglobulin Repertoire in Phage Lambda," Science, 1989, 246, pp. 1275-1281.
Huston et al., "Protein engineering of antibody binding sites: Recovery of specific activity in an anti-digoxin single-chain Fv analogue produced in Escherichia coli," Proc. Natl. Acad. Sci. USA, 1988, 85, pp. 5879-5883.
Inagaki, M., et al. "Naphthalenesulfonamides as Calmodulin Antagonists and Protein Kinase Inhibitors," Mol. Pharmacol., 1986, 29, p. 577-581.
Inman et al., "SB-431542 Is a Potent and Specific Inhibitor of Transforming Growth Factor-β Superfamily Type I Activin Receptor-Like Kinase (ALK) Receptors ALK4, ALK5, and ALK7," Molecular Pharmacology, 2002, 62, pp. 65-74.
Issinger, O.G., "Casein Kinases: Pleiotropic Mediators of Cellular Regulation," Pharmacol Ther., 1993, 59, pp. 1-30.
Joachim, C.L. et al., "Amyloid β-protein deposition in tissues other than brain in Alzheimer's Disease," Nature, 1989, 341(6239), pp. 226-230.
Kloss, B. et al., "Phosphorylation of Period Is Influenced by Cycling Physical Associations of Double-Time, Period, and Timeless in the Drosophila Clock," Neuron, 2001, 30, pp. 699-706.
Kohler and Milstein, "Continuous cultures of fused cells secreting antibody of predefined specificity," Nature, 1975, 256, pp. 495-497.
Kopan, R., et al., "Signal transduction by activated mNotch: Importance of proteolytic processing and its regulation by the extracellular domain," Proc. Natl. Acad. Sci. U.S.A., 1996, 93, pp. 1683-1688.
Kozbor et al., "The production of monoclonal antibodies from human lymphocytes," Immunology Today, 1983, 4(3), p. 72-79.
Kusuda et al., "Sequence Analysis of the cDNA for the Human Casein Kinasse I d (CSNK1D) Gene and Its Chromosomal Localization," Genomics, 1996, 32, pp. 140-143.
Liu, F. et al., "Regulation of cyclin-dependent kinase 5 and casein kinase 1 by metabotropic glutamate receptors," Proc Natl Acad Sci., 2001, 98, pp. 11062-11068.
Liu, S.J. et al., "Overactivation of glycogen synthase kinase-3 by inhibition of phosphoinositol-3 kinase and protein kinase C leads to hyperphosphorylation of tau and impairment of spatial memory," J. Neurochem, 2003, 87, pp. 1333-1344.
Lu et al., Adv. Genet., 2005, 54, pp. 117-142.
Mashhoon et al., "Crystal structure of a conformation-selective caseine kinase-1 inhibitor", J. Biological Chemistry, 2000, vol. 275, No. 26, pp. 20052-20060.
Massillon, D., "Identification of the glycogenic compound 5-iodotubercidin as a general protein kinase inhibitor," Biochem J., 1994, 299 (Pt 1), pp. 123-128.
Matsumura, S. and Takeda, M., "Phosphoprotein kinases from rat liver cytosol," Biochim Biophys Acta. 1972, 289(1), pp. 237-241.
Meggio, F. et al., "Ribofuranosyl-benzimidazole derivatives as inhibitors of casein kinase-2 and casein kinase-1," Eur J Biochem., 1990, 187(1), pp. 89-94.
Meijer, L. et al., "Inhibition of cyclin-dependent kinases, GSK-3β and CK1 by hymenialdisine, a marine sponge constituent," Chem Biol., 2000(1), pp. 51-63.
Meijer, L. et al., Trends Pharmacol Sci., 2004, 25, pp. 471-480.
Miller et al., "RNA Interference in Neuroscience: Progress and Challenges," Cell Mol. Neurobiol., 2005, 25, pp. 1195-1207.
Morrison et al., "Chimeric human antibody molecules: Mouse antigen-binding domains with human constant region domains," Proc. Natl. Acad. Sci., 1984, 81, pp. 6851-6855.
Netzer, W.J., et al., "Gleevec inhibits β-amyloid production but not Notch cleavage," Proc. Natl. Acad. Sci. U.S.A., 2003, 100(21), pp. 12444-12449.
Neuberger et al., "Recombinant antibodies possessing novel effector function," Nature, 1984, 312, pp. 604-608.

(56) References Cited

OTHER PUBLICATIONS

Pastorino, L. et al., "The Carboxyl-Terminus of BACE Contains a sorting Signal that Regulates BACE Trafficking but Not the Formation of Total Aβ," *Mo. Cell Neurosci.*, 2002, 19, pp. 175-185.

Reinhardt, J. et al., "Purification of CK1 by affinity chromatography on immobilized axin", *Protein Expression and Purification*, 2007, vol. 54, pp. 101-109.

Rena et al., "D4476, a cell-permeant inhibitor of CK1, suppresses the site-specific phosphorylation and nuclear exclusion of FOXO1a", *EMBO Reports*, 2004, vol. 5, No. 1, pp. 60-65.

Schwab, C. et al., "Casein kinase 1 delta is associated with pathological accumulation of tau in several neurodegenerative diseases", *Neurobiology of Aging*, vol. 21, 2000, pp. 503-510.

Singh, T.J. et al., "Rapid Alzheimer-like phosphorylation of tau by the synergistic actions of non-proline-depenent protein kinases and GSK-3," *FEBS Lett.*, 1995, 358, pp. 267-272.

Takeda et al., "Construction of chimaeric processed immunoglobulin genes containing mouse variable and human constant region sequences," *Nature*, 1985, 314, pp. 452-454.

Turner, E.J.H. et al., "ATP-dependent vesiculation in red cell membranes from different hereditary stomatocytosis variants," *Br. J. Haematol*, 2003, 120, p. 894-902.

Vancura, A. et al., "A Prenylation Motif Is Require for Plasma Membrane Localization and Biochemical Function of Casein Kinase I in Budding Yeast," *J. Biol Chem.*, 1994, 269, pp. 19271-19278.

Ueno, T., et al., "Immunohistochemical study of cytokeratins in amyloid deposits associated with squamous cell carcinoma and dysplasia in the oral cavity, pharynx and larynx", *Pathology International*, 2003, vol. 53, pp. 265-269.

Walter et al., "Phosphorylation regulation intracellular trafficking of beta-secretase", *J. Biological Chemistry*, 2001, vol. 276, No. 18, pp. 14634-14641.

Walter, J. et al., "Proteolytic Fragments of the Alzheimer's Disease Associated Presenilins-1 and -2 Are Phosphorylated in Vivo by Distinct Cellular Mechanisms," *Biochemistry*, 1998, 37, pp. 5961-5967.

Walter, J., et al., "Phosphorylation of the β-Amyloid Precursor Protein at the Cell Surface by Ectocasein Kinases 1 and 2*," *J. Biol. Chem.*, 2000, vol. 275, No. 31, pp. 23523-23529.

Walter, J. et al., "Induced Release of Cell Surface Protein Kinase Yields CK1- and CK2-like Enzymes in Tandem," *J. Biol. Chem.*, 1996, 271, pp. 111-119.

Ward et al., "Binding activities of a repertoire of single immunoglobulin variable domains secreted from *Escherichia coli*," *Nature*, 1989, 341, pp. 544-546.

Xu, H., et al., "Estrogen reduces neuronal generation of Alzheimer β-amyloid peptides," *Nat. Med.*, 1998, 4, pp. 447-451.

Yasojima et al., "Casein kinase 1 delta mRNA is upregulated in Alzheimer disease brain", *Brain Research*, 2000, vol. 865, pp. 116-120.

Yokoyama, T. et al., "Characterization of (−) Matairesinol as a Potent Inhibitor of Casein Kinase I in Vitro," *Biol Pharm Bull.*, 2003, (3), pp. 371-374.

Zhai, L. et al., "Casein Kinase Iγ Subfamily," *J. Biol. Chem.*, 1995, vol. 270, pp. 12717-12724.

International Search Report of International Application No. PCT/US2007/022519, prepared by the International Searching Authority, dated Oct. 7, 2008, 4 pages.

\* cited by examiner

ORGANIC COMPOUNDS

CROSS-REFERENCE TO RELATED APPLICATIONS

This application is a U.S. National Stage application of PCT/US2015/010901, filed on Jan. 9, 2015, which claims priority to U.S. Provisional Application No. 61/925,608 filed Jan. 9, 2014, the contents of which are hereby incorporated by reference in their entirety.

TECHNICAL FIELD

The present invention relates to novel compounds useful as CK1 inhibitors, pharmaceutical compositions comprising said compounds and methods for inhibiting CK1 as well as methods of treatment of CK1 related disorders, comprising administering a therapeutically effective amount of a CK1 inhibitor to a patient in need thereof.

BACKGROUND OF THE INVENTION

Alzheimer's disease (AD) is an irreversible, progressive brain disease characterized by the loss of cognitive functioning, e.g., memory and reasoning, and behavioral abilities. AD is estimated to affect more than 25 million people in the world and is reported in the 2010 World Alzheimer Report to have annual societal costs of US$604 billion, or 1% of the aggregated worldwide Gross Domestic Product (GDP). Existing AD medications aim to treat symptoms of AD only and do so rather poorly. Existing AD medications do not address the progression of the disease. New therapeutic agents that slow (or reverse) the disease and that target multiple aspects of the disorder are urgently needed.

Studies have shown that the etiology of AD includes a range of clear genetic predispositions involving amyloid precursor protein (APP), Tau phosphorylation, gamma-secretase (GS), apolipoprotein E (ApoE) and genes involved in circadian rhythms. There is strong evidence which indicates the importance of Tau hyper-phosphorylation, excessive amyloid beta (Aβ) formation and desynchrony of circadian rhythms in Alzheimer's disease. There is also clear evidence of a cell loss in the suprachiasmatic nucleus, the brain region involved in regulating circadian rhythms that coincides with development of the dementia stage of AD. AD patients suffer a plethora of symptoms including serious and progressive cognitive decline, sleep disturbances and agitation.

Casein Kinase 1 is a member of a unique class of protein serine/threonine kinases that are only distantly related to other kinase families. Comparing CK1 sequence identities to other kinase families, glycogen synthase kinase 3 (GSK3) is the closest related kinase outside the CK1 family and is only 20% identical in the catalytic domain. The CK1 family has seven isoforms with various splice variants. The role of CK1 in AD is substantially documented in recent reviews. See Buee et al., *Brain Res. Rev.* (2000) 33(1):95-130; See also Perez et al., *Med. Res. Rev.* (2010) 31(6):924-54. It has been observed that CK1 delta mRNA is elevated 30-fold in the hippocampus of AD patients' brains. Yasojima et al., *Brain Res.* (2000) 865(1):116-20. The beneficial effect of CK1 inhibitors to reverse Aβ formation has also been shown. Flajolet et al., *Proc. Natl. Acad. Sci. U.S.A.* (2007) 104(10): 4159-64. With regard to the phosphorylation of various Tau forms, there are multiple sites of phosphorylation of Tau and a number of putative Tau kinases are involved. Although the role of various kinases in this process is complex, the importance of critical priming kinases is generally accepted as driving the hyper-phosphorylation co-incident with the formation of paired helical filaments (PHF) that are the universal pathology associated with AD. It is well documented that CK1 is a "major Tau kinase" with priming functions and is associated with paired helical filaments (PHF). Hanger et al., *J. Biol. Chem.* (2007) 282(32):23645-54. Most importantly, there is substantial evidence for a fundamental role of CK1 controlling circadian rhythm and metabolic state through phosphorylation and regulation of a series of transcription factors including CLOCK, BMAL-1, and Perl-3; with CK1 and CK2 collectively considered the "clock genes". Ebisawa T., *J. Pharmacol. Sci.* (2007) 103 (2):150-4. CK1 delta and epsilon gene variations are also associated with circadian rhythms changes.

Highly specific CK1 inhibitors have been developed and have served to further validate the role of CK1 in AD related pathologies. Several examples of potent and selective inhibitors are known. Using potent and selective CK1 inhibitors in rodent and monkey animal models, profound influences on phase shifts in circadian rhythms are discovered that substantially validate the hypothesis of CK1 involvement in the biological clock. Sprouse et al., *Psychopharmacology* (Berl) (2010) 210(4):569-76; Sprouse et al., *Psychopharmacology* (Berl) (2009) 204(4):735-42. All of these studies therefore support the critical role of CK1 as therapeutic target in AD.

In view of the important role of CK1, further potent and selective CK1 inhibitors are needed in the fight against AD and other CK1 related diseases.

SUMMARY OF THE INVENTION

The current invention provides novel compounds useful as CK1 inhibitors. Therefore, in the first aspect, the invention provides a compound of Formula I:

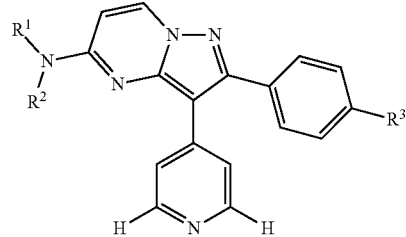

Formula I wherein:
(i) R³ is halo (e.g., fluoro); and
(ii) R¹ and R² together form a piperazine ring wherein said piperazine is optionally substituted with a $C_{1-6}$alkyl;
in free or salt form.

In a further embodiment of the first aspect, the invention provides the compound of Formula I as follows:
1.1. the compound of Formula I, wherein the piperazine ring is substituted with a $C_{1-6}$alkyl (e.g., methyl), for example 4-methylpiperazin-1-yl;
1.2. the compound of Formula I or formula 1.1, wherein R³ is fluoro;

1.3. the compound of Formula I, which is:

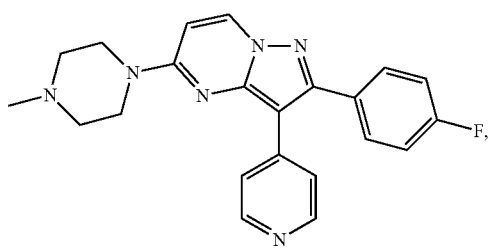 [SMILES: CN1CCN(c2ccn3nc(-c4ccc(F)cc4)c(-c4ccncc4)c3n2)CC1]

in free or salt form.

In the second aspect, the invention provides a compound of Formula II:

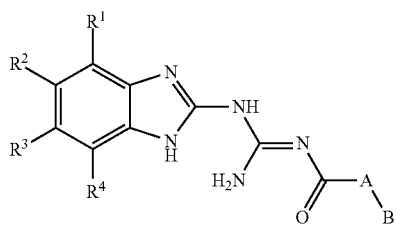

Formula II wherein:
   (i) $R^1$, $R^2$, $R^3$ and $R^4$ are independently selected from the group consisting of H, $C_{1-6}$alkyl (e.g., methyl) and halo (e.g., chloro);
   (ii) A is $C_{1-4}$alkylene (e.g., methylene or ethylene);
   (iii) B is a monocyclic or bicyclic aryl or heteroaryl (e.g., phenyl, naphthyl or pyridyl), optionally substituted with —N(H)($R^a$), wherein $R^a$ is —C(O)—$C_{1-6}$alkyl (e.g., —C(O)$CH_3$);
in free or salt form.

In a further embodiment of the second aspect, the invention provides the compound of Formula II as follows:
   2.1. the compound of Formula II, wherein $R^1$, $R^2$, $R^3$ and $R^4$ are independently selected from the group consisting of H, $C_{1-6}$alkyl (e.g., methyl) and halo (e.g., chloro);
   2.2. the compound of Formula II or formula 2.1, wherein $R^1$, $R^2$, $R^3$ and $R^4$ are independently H;
   2.3. the compound of Formula II or formula 2.1 or 2.2, wherein $R^1$, $R^2$, $R^3$ and $R^4$ are independently $C_{1-6}$alkyl (e.g., methyl);
   2.4. the compound of Formula II or any one of formulae 2.1-2.3, wherein $R^1$, $R^2$, $R^3$ and $R^4$ are independently halo (e.g., chloro);
   2.5. the compound of Formula II or any one of formulae 2.1-2.4 wherein $R^3$ and $R^4$ are independently H or methyl;
   2.6. the compound of Formula II or any one of formulae 2.1-2.5, wherein $R^3$ is halo (e.g., chloro) or $C_{1-6}$alkyl (e.g., methyl);
   2.7. the compound of Formula II or any one of formulae 2.1-2.6, wherein A is $C_{1-4}$alkylene (e.g., methylene or ethylene);
   2.8. the compound of Formula II or any one of formulae 2.1-2.6, wherein A is methylene;
   2.9. the compound of Formula II or any one of formulae 2.1-2.6, wherein A is ethylene;
   2.10. the compound of Formula II or any one of formulae 2.1-2.9, wherein B is a mono-cyclic or bicyclic aryl or heteroaryl (e.g., phenyl, naphthyl or pyridyl), optionally substituted with —N(H)($R^a$), wherein $R^a$ is —C(O)—$C_{1-6}$alkyl (e.g., —C(O)$CH_3$);
   2.11. the compound of Formula II or any one of formulae 2.1-2.9, wherein B is a monocyclic or bicyclic heteroaryl (e.g., pyridyl);
   2.12. the compound of Formula II or any one of formulae 2.1-2.9, wherein B is pyridyl (e.g., pyrid-3-yl);
   2.13. the compound of Formula II or any one of formulae 2.1-2.9, wherein B is a monocyclic or bicyclic aryl (e.g., phenyl or naphthyl) optionally substituted with —N(H)($R^a$), wherein $R^a$ is —C(O)—$C_{1-6}$alkyl (e.g., —C(O)$CH_3$);
   2.14. the compound of Formula II or any one of formulae 2.1-2.9, wherein B is a monocyclic or bicyclic aryl (e.g., phenyl or naphthyl) substituted with —N(H)($R^a$), wherein $R^a$ is —C(O)—$C_{1-6}$alkyl (e.g., —C(O)$CH_3$);
   2.15. the compound of Formula II or any of the foregoing formulae, wherein:
      (i) $R^1$, $R^2$, $R^3$ and $R^4$ are H;
      (ii) A is $C_{1-4}$alkylene (e.g., methylene);
      (iii) B is a monocyclic or bicyclic heteroaryl (e.g., pyridyl, for example pyrid-3-yl);
   2.16. the compound of Formula II, selected from the group consisting of:

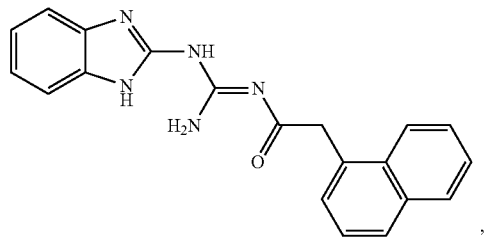

,

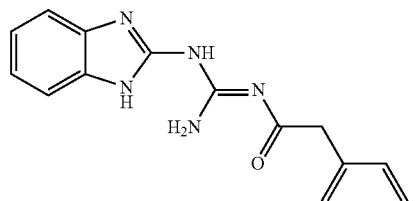

,

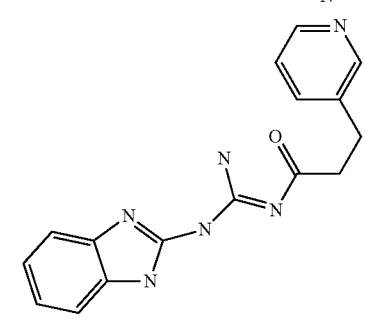

,

-continued

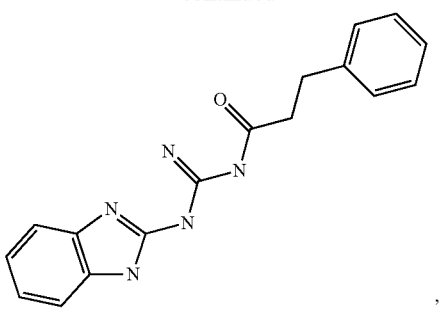
,

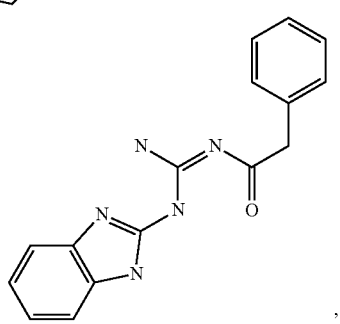
,

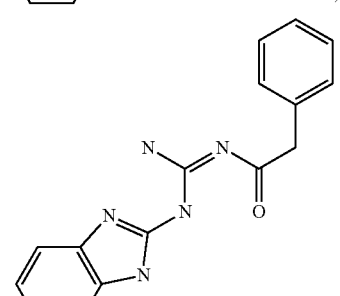
,

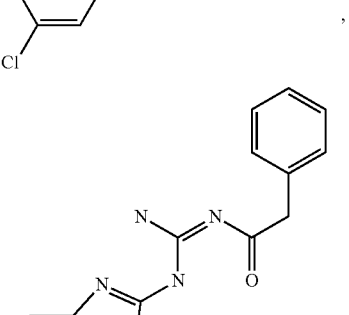
,

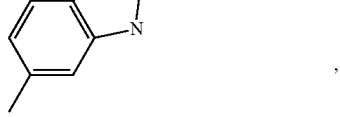
and

-continued

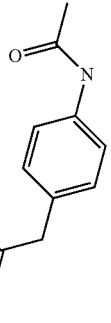
;

in free or salt form.

In the third aspect, the invention provides a compound of Formula III:

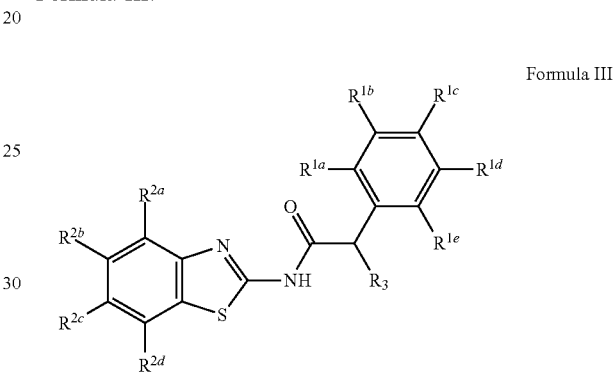

Formula III wherein:
(i) $R^{1a}$, $R^{1b}$, $R^{1c}$, $R^{1d}$ and $R^{1e}$ are independently selected from the group consisting of H, halo (e.g., bromo or fluoro), hydroxy and —N($R^4$)($R^5$);
(ii) $R^{2a}$, $R^{2b}$, $R^{2c}$ and $R^{2d}$ are independently selected from the group consisting of H, $C_{1-4}$alkyl (e.g., methyl, ethyl, tert-butyl, alkynyl, i.e., —CCH) and $C_{1-4}$alkylcarbonyl (e.g., —C(O)—CH$_3$), provided $R^{2a}$ is not methyl;
(iii) $R^3$ is selected from the group consisting of H, hydroxy and —NH$_2$;
(iv) $R^4$ and $R^5$ are independently selected from the group consisting of H, $C_{1-4}$alkyl (e.g., methyl) and $C_{1-4}$alkylcarbonyl (e.g., —C(O)—CH$_3$);
(v) provided that when $R^{1a}$, $R^{1b}$, $R^{1c}$, $R^{1d}$, $R^{1e}$ and a $R^3$ are H, then $R^{2a}$, $R^{2b}$, $R^{2c}$ and $R^{2d}$ are independently H or an unsaturated $C_{2-4}$alkyl (e.g., alkynyl);

in free or salt form.

In a further embodiment of the third aspect, the invention provides the compound of Formula III as follows:
3.1. the compound according to Formula III, wherein $R^{1a}$, $R^{1b}$, $R^{1c}$, $R^{1d}$ and $R^{1e}$ are independently selected from the group consisting of H, halo (e.g., bromo or fluoro), hydroxy and —N($R^4$)($R^5$);
3.2. the compound according to Formula III or formula 3.1, wherein $R^{1a}$, $R^{1b}$, $R^{1c}$, $R^{1d}$ and $R^{1e}$ are independently H;
3.3. the compound according to Formula III or formula 3.1, wherein $R^{1a}$, $R^{1b}$, $R^{1c}$, $R^{1d}$ and $R^{1e}$ are all H, or $R^{1a}$, $R^{1b}$, $R^{1d}$ and $R^{1e}$ are all H and $R^{1c}$ is selected from the group consisting of halo (e.g., bromo or fluoro), hydroxy and —N($R^4$)($R^5$);

3.4. the compound according to Formula III or formula 3.1, 3.2 or 3.3, wherein $R^{1a}$, $R^{1b}$, $R^{1c}$, $R^{1d}$ and $R^{1e}$ are independently halo (e.g., bromo or fluoro);

3.5. the compound according to Formula III or any one of formulae 3.1-3.4, wherein $R^{1a}$, $R^{1b}$, $R^{1c}$, $R^{1d}$ and $R^{1e}$ are independently hydroxy;

3.6. the compound according to Formula III or any one of formulae 3.1-3.5, wherein $R^{1a}$, $R^{1b}$, $R^{1c}$, $R^{1d}$ and $R^{1e}$ are independently —N($R^4$)($R^5$);

3.7. the compound according to Formula III, wherein $R^{1a}$, $R^{1b}$, $R^{1d}$ and $R^{1e}$ are H and $R^{1c}$ is selected from the group consisting of halo (e.g., bromo or fluoro), hydroxy and —N($R^4$)($R^5$), for example $R^{1c}$ is bromo, fluoro, hydroxy, dimethylamino or —NHC(O)CH$_3$;

3.8. the compound according to Formula III or any one of formulae 3.6 or 3.7, wherein $R^4$ and $R^5$ are independently selected from the group consisting of H, $C_{1-4}$alkyl (e.g., methyl), and $C_{1-4}$alkylcarbonyl (e.g., —C(O)—CH$_3$);

3.9. the compound according to Formula III or formula 3.6, 3.7 or 3.8, wherein $R^4$ or $R^5$ is H;

3.10. the compound according to Formula III or any one of formulae 3.6-3.9, wherein $R^4$ or $R^5$ is $C_{1-4}$alkyl (e.g., methyl);

3.11. the compound according to Formula III or any one of formulae 3.6-3.10, wherein $R^4$ or $R^5$ is $C_{1-4}$alkylcarbonyl (e.g., —C(O)—CH$_3$);

3.12. the compound according to Formula III or any one of formulae 3.6-3.10, wherein $R^4$ is H and $R^5$ is $C_{1-4}$alkyl (e.g., methyl);

3.13. the compound according to Formula III or formula 3.6, 3.7 or 3.8, wherein $R^4$ and $R^5$ are both $C_{1-4}$alkyl (e.g., methyl);

3.14. the compound according to Formula III or any one of formulae 3.1-3.13, wherein $R^{1a}$, $R^{1b}$, $R^{1c}$, $R^{1d}$ and $R^{1e}$ are independently selected from the group consisting of halo (e.g., bromo or fluoro), hydroxy and —N($R^4$)($R^5$);

3.15. the compound according to Formula III or any one of formulae 3.1-3.14, wherein $R^{2a}$, $R^{2b}$, $R^{2c}$ and $R^{2d}$ are independently selected from the group consisting of H, $C_{1-4}$alkyl (e.g., methyl, ethyl, tert-butyl or alkynyl, i.e., —CCH) and $C_{1-4}$alkylcarbonyl (e.g., —C(O)—CH$_3$), provided $R^{2a}$ is not methyl;

3.16. the compound according to Formula III or any one of the preceding formulae, wherein $R^{2a}$, $R^{2b}$, $R^{2c}$ and $R^{2d}$ are independently H;

3.17. the compound according to Formula III or any one of the preceding formulae, wherein $R^{2a}$, $R^{2b}$, $R^{2c}$ and $R^{2d}$ are independently H or $C_{1-4}$alkyl (e.g., methyl, ethyl, tert-butyl or alkynyl, i.e., —CCH), provided $R^{2a}$ is not methyl;

3.18. the compound according to Formula III or any one of the preceding formulae, wherein $R^{2a}$, $R^{2b}$, $R^{2c}$ and $R^{2d}$ are independently H or $C_{1-4}$alkylcarbonyl (e.g., —C(O)—CH$_3$);

3.19. the compound according to Formula III or any one of the preceding formulae, wherein $R^{2a}$ is H;

3.20. the compound according to Formula III or any one of the preceding formulae, wherein $R^2$ is selected from the group consisting of $C_{1-4}$alkyl (e.g., methyl, ethyl, tert-butyl or alkynyl, i.e., —CCH) and $C_{1-4}$alkylcarbonyl (e.g., —C(O)—CH$_3$);

3.21. the compound according to Formula III or any one of the preceding formulae, wherein $R^{2c}$ is $C_{1-4}$alkyl (e.g., methyl, ethyl, tert-butyl or alkynyl, i.e., —CCH);

3.22. the compound according to Formula III or any one of the preceding formulae, wherein $R^{2d}$ is $C_{1-4}$alkyl (e.g., alkynyl, i.e., —CCH);

3.23. the compound according to Formula III or any one of the preceding formulae, wherein $R^3$ is selected from the group consisting of H, hydroxy and —NH$_2$;

3.24. the compound according to Formula III or any one of the preceding formulae, wherein $R^3$ is H;

3.25. the compound according to Formula III or any one of the preceding formulae, wherein $R^3$ is —OH;

3.26. the compound according to Formula III or any one of the preceding formulae, wherein $R^3$ is —NH$_2$;

3.27. the compound according to Formula III, wherein:
(i) $R^{1a}$, $R^{1b}$, $R^{1d}$ and $R^{1e}$ are H and $R^{1c}$ is —N($R^4$)($R^5$);
(ii) $R^{2a}$, $R^{2b}$ and $R^{2d}$ are H and $R^{2c}$ is $C_{1-4}$alkyl (e.g., ethyl);
(iii) $R^3$ is H;
(iv) $R^4$ is H and $R^5$ is $C_{1-4}$alkylcarbonyl (e.g., —C(O)—CH$_3$);

3.28. the compound according to Formula III selected from any of the following:

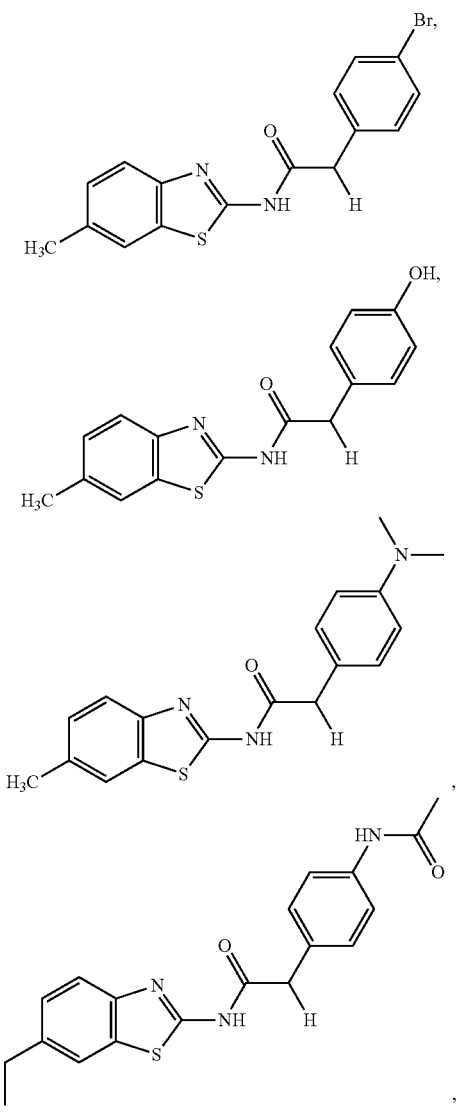

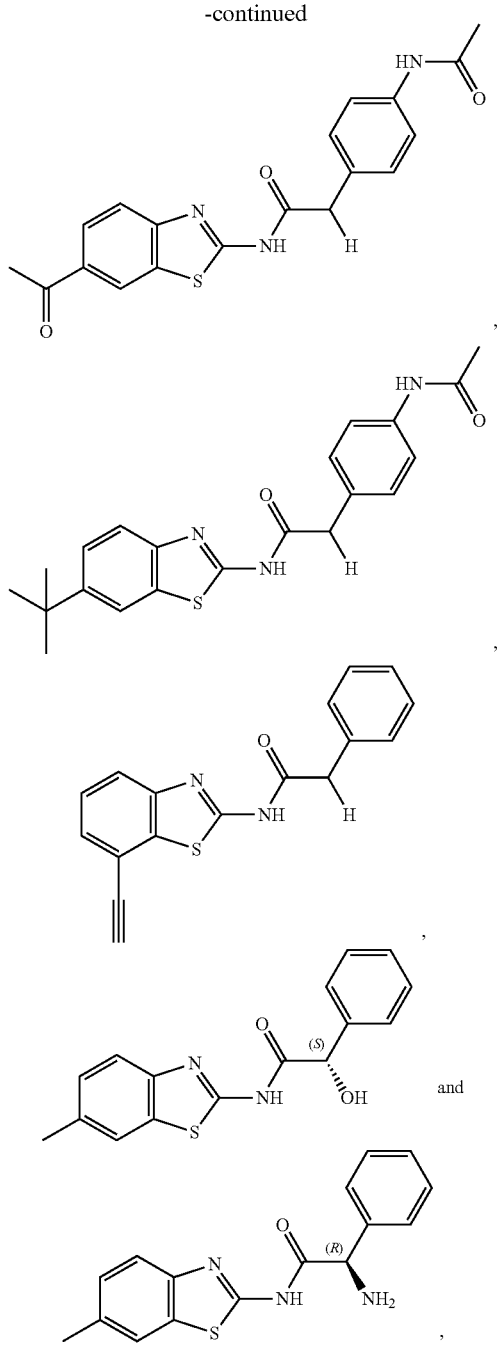

in free or salt form.

The compounds of the invention are useful as Casein Kinase 1 (CK1) inhibitors, particularly CK1 delta (CK1δ) and/or CK1 epsilon (CK1ε) inhibitors. CK1 delta mRNA has been shown to be elevated by 30-fold in the hippocampus of Alzheimer's disease patients' brain. The beneficial effect of CK1 inhibitors to reverse Aβ formation has also been established. Further, CK1 has been shown to be a major Tau kinase with priming functions and is associated with paired helical filaments (PHF), which are the universal pathology associated with Alzheimer's Disease. CK1 overexpression has also been shown to increase amyloid beta formation while CK1 inhibitors lower amyloid beta formation. There is also evidence of CK1 controlling circadian rhythm and metabolic state through phosphorylation and regulation of a series of transcription factors including CLOCK, BMAL-1 and Perl-3. In particular, CK1δ and CK1ε are associated with circadian rhythms changes. Therefore, the role of CK1 in Alzheimer's disease is well documented and CK1 inhibitors of the invention are particularly useful as a therapeutic agent.

Therefore, in the fourth aspect, the invention provides a pharmaceutical composition (Composition 1) comprising a CK1 inhibitor of the current invention as hereinbefore described, in free or pharmaceutically acceptable salt form, in combination or association with a pharmaceutically acceptable diluent or carrier.

In the fifth aspect, the invention provides a method (Method 1) for inhibiting CK1 activity, e.g., inhibiting CK1δ and/or CK1ε activity, comprising contacting CK1, particularly CK1δ and/or CK1ε, with any one of the compounds of the current invention as described herein, or a pharmaceutical composition of the current invention.

In the sixth aspect, the invention provides a method (Method 2) for the treatment or prophylactic treatment, control or management of a disorder that can be benefited from CK1 inhibition, such as disorders related to abnormally hyperphosphorylated Tau state, e.g., Alzheimer's disease, cancer, attention deficit hyperactive disorder (ADHD), disorder associated with the desynchrony of circadian rhythms, for example sleep disorders (e.g., advanced sleep phase syndrome or delayed shift phase syndrome, jet lag syndrome, shift work sleep disorder), mood disorders, depressive disorders, e.g., depression, bipolar disorder (bipolar I and bipolar II disorder), or desynchrony of circadian rhythms associated with Alzheimer's disease, dementia, Down syndrome, frontotemporal dementia with Parkinsonism linked to chromosome 17 (FTDP-17), amyotrophic lateral sclerosis, corticobasal degeneration, dementia pugilistica, Pick disease, tangle-only dementia, acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, AIDS-induced dementia, vascular dementia, mixed dementias, age-associated memory impairment, Huntington's Chorea, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, narcolepsy, autism, Asperger's disease, and conduct disorder in a mammal, comprising administering to a subject in need thereof an effective amount of a CK1 inhibitor of the current invention as hereinbefore described, preferably a CK1δ and/or CK1ε inhibitor, in free or pharmaceutically acceptable salt form.

In the seventh aspect, the invention provides a pharmaceutical composition (Composition 1) comprising a CK1 inhibitor of the current invention as hereinbefore described, in free or pharmaceutically acceptable salt form, in combination or association with a pharmaceutically acceptable diluent or carrier, for use (in the manufacture of a medicament) for the treatment or prophylactic treatment, control or management of a disorder that can be benefited from CK1 inhibition, such as disorders related to abnormally hyperphosphorylated Tau state, e.g., Alzheimer's disease, cancer, attention deficit hyperactive disorder (ADHD), disorder associated with the desynchrony of circadian rhythms, for example sleep disorders (e.g., advanced sleep phase syndrome or delayed shift phase syndrome, jet lag syndrome, shift work sleep disorder), mood disorders, depressive disorders, e.g., depression, bipolar disorder (bipolar I and bipolar II disorder), or desynchrony of circadian rhythms associated with Alzheimer's disease, dementia, Down syndrome, frontotemporal dementia with Parkinsonism linked to chromosome 17 (FTDP-17), amyotrophic lateral sclerosis, corticobasal degeneration, dementia pugilistica, Pick disease, tangle-only dementia, acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, AIDS-induced dementia, vascular dementia, mixed dementias, age-associated memory impairment, Huntington's Chorea, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, narcolepsy, autism, Asperger's disease, and conduct disorder in a mammal.

In the eighth aspect, the invention provides use of a CK1 inhibitor of the current invention, in free or pharmaceutically acceptable salt form, (in the manufacture of a medicament) for the treatment or prophylactic treatment, control or management of a disorder that can be benefited from CK1 inhibition, such as disorders related to abnormally hyperphosphorylated Tau state, e.g., Alzheimer's disease, cancer, attention deficit hyperactive disorder (ADHD), disorder associated with the desynchrony of circadian rhythms, for example sleep disorders (e.g., advanced sleep phase syndrome or delayed shift phase syndrome, jet lag syndrome, shift work sleep disorder), mood disorders, depressive disorders, e.g., depression, bipolar disorder (bipolar I and bipolar II disorder), or desynchrony of circadian rhythms associated with Alzheimer's disease, dementia, Down syndrome, frontotemporal dementia with Parkinsonism linked to chromosome 17 (FTDP-17), amyotrophic lateral sclerosis, corticobasal degeneration, dementia pugilistica, Pick disease, tangle-only dementia, acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, AIDS-induced dementia, vascular dementia, mixed dementias, age-associated memory impairment, Huntington's Chorea, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, narcolepsy, autism, Asperger's disease, and conduct disorder in a mammal.

In one embodiment of the sixth, seventh and eighth aspects, the disorder is selected from the group consisting of Alzheimer's disease, attention deficit hyperactive disorder (ADHD), disorder associated with the desynchrony of circadian rhythms, for example sleep disorders, e.g., advanced sleep phase syndrome or delayed shift phase syndrome), mood disorders, depressive disorders, e.g., depression, bipolar disorder, or desynchrony of circadian rhythms associated with Alzheimer's disease. In another embodiment, the disorder is Alzheimer's disease.

In the ninth aspect, the invention provides CK1 tracer compounds useful for Gamma radiation-based imaging. Two commonly employed gamma radiation-based imaging techniques are Positron Emission Tomography (referred to as PET) and Single Photon Emission Computed Tomography (referred to as SPECT). Therefore, CK1 tracer compounds of the current invention comprise (i) a CK1 inhibitor of the current invention as hereinbefore described, in free or pharmaceutically acceptable salt form; and (ii) a radionuclide chemically bound to said CK1 inhibitor. Examples of isotopes useful in gamma radiation-based imaging include Carbon-11 (referred to as 11C or C11), Fluorine-18 (referred to as 18F or F18), Technetium-99m (referred to as 99mTc or Tc99m), Indium-111 (referred to as 111In or In111) and Iodine-123 (referred to as 123I or I123).

Therefore, in a further embodiment of the ninth aspect, the radionuclide is selected from Carbon-11 (referred to as $^{11}$C or C$^{11}$), Fluorine-18 (referred to as $^{18}$F or F$^{18}$), Technetium-99m (referred to as $^{99}$mTc or Tc$^{99}$m), Indium-111 (referred to as $^{111}$In or In$^{111}$) and Iodine-123 (referred to as $^{123}$I or I$^{123}$), preferably $^{11}$C or $^{18}$F. For example, the CK1 tracer compound of the invention is the compound of Formula I selected from any of the following:

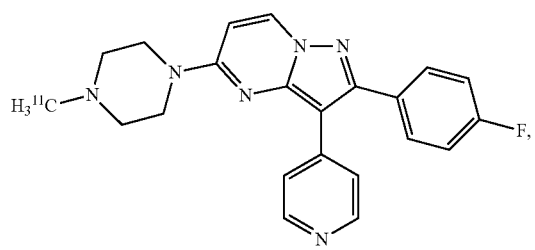

-continued

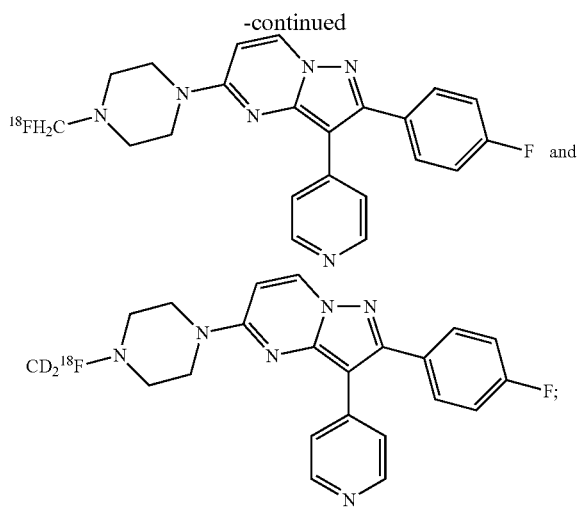

in free or salt form.

In another embodiment of the ninth aspect, the invention provides CK1 tracer compounds comprising halonium salt of a compound selected from the following:
a) a compound of Formula I:

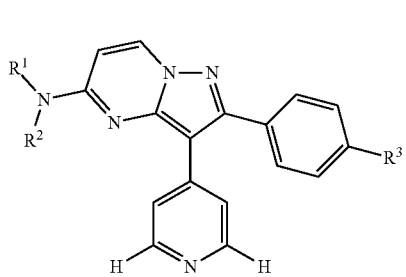
Formula I wherein:
(i) $R^3$ is $F^{18}$; and
(ii) $R^1$ and $R^2$ together form a piperazine ring wherein said piperazine is optionally substituted with a $C_{1-6}$alkyl;
in free or salt (e.g., pharmaceutically acceptable salt) form;
b) a compound of Formula II:

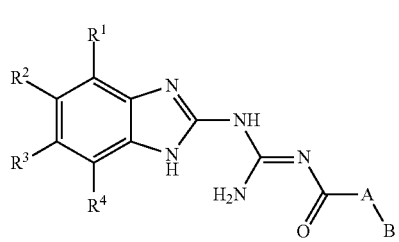
Formula II wherein:
(i) $R^1$, $R^2$, $R^3$ and $R^4$ are independently $F^{18}$ or $I^{123}$;
(ii) A is $C_{1-4}$alkylene (e.g., methylene or ethylene);
(iii) B is a monocyclic or bicyclic aryl or heteroaryl (e.g., phenyl, naphthyl or pyridyl), optionally substituted with —N(H)($R^a$), wherein $R^a$ is —C(O)—$C_{1-6}$alkyl (e.g., —C(O)CH$_3$);
in free or salt (e.g., pharmaceutically acceptable salt) form; and c) a compound of Formula III:

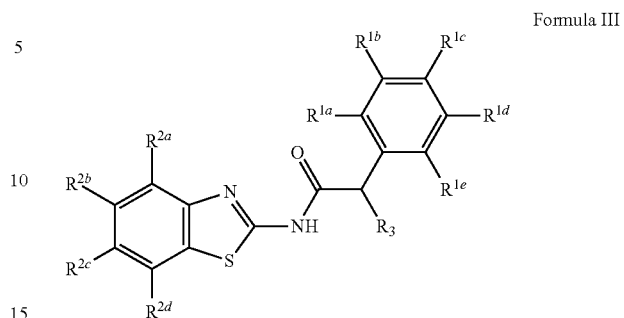
Formula III wherein:
(i) $R^{1a}$, $R^{1b}$, $R^{1c}$, $R^{1d}$ and $R^{1e}$ are independently $F^{18}$;
(ii) $R^{2a}$, $R^{2b}$, $R^{2c}$ and $R^{2d}$ are independently selected from the group consisting of H, $C_{1-4}$alkyl (e.g., methyl, ethyl, tert-butyl, alkynyl, i.e., —CCH) and $C_{1-4}$alkyl-carbonyl (e.g., —C(O)—CH$_3$), provided $R^{2a}$ is not methyl;
(iii) $R^3$ is selected from the group consisting of H, hydroxy and —NH$_2$;
(iv) provided that when $R^{1a}$, $R^{1b}$, $R^{1c}$, $R^{1d}$ and $R^{1e}$ and $R^3$ are H, then $R^{2a}$, $R^{2b}$, $R^{2c}$ and $R^{2d}$ are independently H or an unsaturated $C_{2-4}$alkyl (e.g., alkynyl);
in free or salt (e.g., pharmaceutically acceptable) form.

In another embodiment of the ninth aspect, the invention provides CK1 tracer compounds comprising a compound selected from the following:
a) a compound of Formula I:

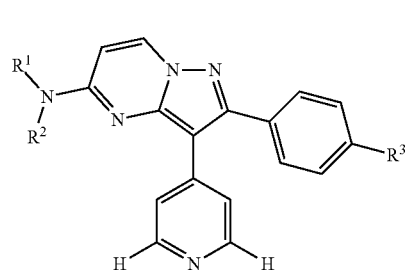
Formula I wherein:
(iii) $R^3$ is $F^{18}$; and
(iv) $R^1$ and $R^2$ together form a piperazine ring wherein said piperazine is optionally substituted with a $C_{1-6}$alkyl;
in free or salt (e.g., pharmaceutically acceptable salt) form;
b) a compound of Formula II:

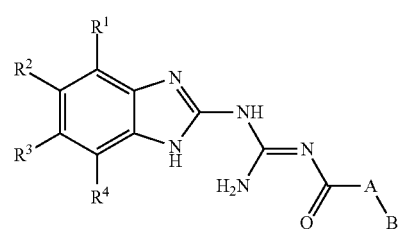
Formula II wherein:
(iv) $R^1$, $R^2$, $R^3$ and $R^4$ are independently $F^{18}$ or $I^{123}$;
(v) A is $C_{1-4}$alkylene (e.g., methylene or ethylene);
(vi) B is a monocyclic or bicyclic aryl or heteroaryl (e.g., phenyl, naphthyl or pyridyl), optionally substituted with —N(H)($R^a$), wherein $R^a$ is —C(O)—$C_{1-6}$alkyl (e.g., —C(O)$CH_3$);

in free or salt (e.g., pharmaceutically acceptable salt) form; and c) a compound of Formula III:

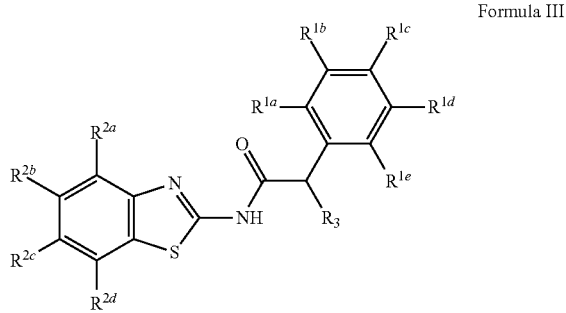

Formula III wherein:
$R^{1a}$, $R^{1b}$, $R^{1c}$, $R^{1d}$ and $R^{1e}$ are independently $F^{18}$;
(vi) $R^{2a}$, $R^{2b}$, $R^{2a}$ and $R^{2d}$ are independently selected from the group consisting of H, $C_{1-4}$alkyl (e.g., methyl, ethyl, tert-butyl, alkynyl, i.e., —CCH) and $C_{1-4}$alkyl-carbonyl (e.g., —C(O)—$CH_3$), provided $R^{2a}$ is not methyl;
(vii) $R^3$ is selected from the group consisting of H, hydroxy and —$NH_2$;
(viii) provided that when $R^{1a}$, $R^{1b}$, $R^{1c}$, $R^{1d}$, $R^{1e}$ and $R^3$ are H, then $R^{2a}$, $R^{2b}$, $R^{2c}$ and $R^{2d}$ are independently H or an unsaturated $C_{2-4}$alkyl (e.g., alkynyl);

in free or salt (e.g., pharmaceutically acceptable) form.

DETAILED DESCRIPTION OF THE INVENTION

It is to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication which might be used in connection with the invention.

As used herein and in the appended claims, the singular forms "a", "an", and "the" include plural reference unless the context clearly dictates otherwise. Thus, for example, reference to the "antibody" is a reference to one or more antibodies and equivalents thereof known to those skilled in the art, and so forth.

The term "CK1" refers to the polypeptide Casein Kinase 1. The term refers to any and all forms of this polypeptide including, but not limited to, homologs, partial forms, isoforms, precursor forms, the full length polypeptide, fusion proteins containing the CK1 sequence or fragments of any of the above, from human or any other species. Numerous isoforms of CK1 have been identified and include, but are not limited to $\alpha$, $\gamma1$, $\gamma2$, $\gamma3$, $\delta$, $\epsilon1$, $\epsilon2$, and $\epsilon3$ isoforms. CK1 and its various isoforms are familiar to one of skill in the art as they have been disclosed in the art. It is also contemplated that the term refers to CK1 isolated from naturally occurring sources of any species such as genomic DNA libraries as well as genetically engineered host cells comprising expression systems, or produced by chemical synthesis using, for instance, automated peptide synthesizers or a combination of such methods. Means for isolating and preparing such polypeptides are well understood in the art.

If not otherwise specified or clear from context, the following terms as used herein have the following meetings:

a. "Alkyl" as used herein is a saturated or unsaturated hydrocarbon moiety, preferably saturated, preferably one to six carbon atoms in length, in some instance one to four carbon atoms in length, which may be linear or branched, and may be optionally substituted, e.g., mono-, di-, or tri-substituted, e.g., with halogen (e.g., chloro or fluoro) or hydroxy.

b. "Cycloalkyl" as used herein is a fully or partially saturated or unsaturated nonaromatic hydrocarbon moiety, preferably comprising three to nine carbon atoms, at least some of which form a nonaromatic mono- or bicyclic, or bridged cyclic structure, and which may be optionally substituted, e.g., with halogen (e.g., chloro or fluoro) or hydroxy.

c. "Aryl" as used herein is a monocyclic or bicyclic aromatic hydrocarbon, preferably phenyl, optionally substituted, e.g., with alkyl (e.g., methyl), halogen (e.g., chloro or fluoro), haloalkyl (e.g., trifluoromethyl) or hydroxy.

d. "Heteroaryl" as used herein is a monocyclic or bicyclic aromatic moiety wherein one or more of the atoms making up the aromatic ring is sulfur, oxygen or nitrogen rather than carbon, e.g., pyridyl or thiadiazolyl, which may be optionally substituted, e.g., with alkyl, halogen, haloalkyl or hydroxy.

e. "Optionally substituted" is intended to be substituted or unsubstituted. In one particular embodiment, the substituent is unsubstituted. In another embodiment, the substituent is substituted. For example, the phrase "piperazine is optionally substituted with a $C_{1-6}$alkyl" is intended to cover unsubstituted piperazine or a piperazine substituted with a $C_{1-6}$alkyl.

The phrase "CK1 inhibitors of the invention" or "the compounds of the invention" refers to any of the compounds disclosed herein, particularly the compounds of formulae I, II and III or any of formulae 1.1-1.3, 2.1-2.16 and 3.1-3.28, in free or salt form. These compounds preferably inhibit CK1, particularly CK1δ and/or CK1ε with a Ki of less than 2 μM, preferably less than 500 nM, more preferably less than 100 nM as described or similarly described in Example 14 or inhibit 50% of CK1 at 10 μM as described or similarly described in Example 15.

The compounds of the invention may exist in free or salt form, e.g., as acid addition salts. In this specification unless otherwise indicated language such as compounds of the invention is to be understood as embracing the compounds in any form, for example free or acid addition salt form, or where the compounds contain acidic substituents, in base addition salt form. The compounds of the invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

The compounds of the invention may in some cases also exist in prodrug form. For example when the compounds contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of compounds of the invention which have hydroxy substituents) or alcohols (in the case of compounds of the invention which have carboxy substituents) which are themselves physiologically tolerable at doses to be administered. As will be appreciated the term thus embraces conventional pharmaceutical prodrug forms.

Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

As will be appreciated by those skilled in the art, the compounds of the invention, for example, the acyl guanidine compounds of Formula II, may exhibit tautomerization. Therefore, the compounds of the invention are to be understood as embracing both the structures as set forth herein (e.g., the compounds of formula 2.16) as well as their tautomeric variants (e.g., isomers in which the N—N double bond of the guanidine group is located in each possible position).

The words "treatment" and "treating" are to be understood accordingly as embracing treatment or amelioration of symptoms of disease as well as treatment of the cause of the disease.

"Subject" refers to any human or nonhuman organism.

It is contemplated herein that any compound with CK1 inhibitory activity, and not necessarily only those compounds that specifically inhibit only CK1, may prove to be useful therapeutics. For example, mixed CK1 inhibitors (e.g., compounds that can inhibit some isoforms of CK1 but not others) may be useful in the instant invention. Preferably, the compounds of the invention are the compounds that preferentially inhibit CK1$\delta$ and/or CK1$\epsilon$, over the other CK1 isoforms.

It is contemplated herein that possible CK1 inhibitors may be metabolites of compounds disclosed herein. It is further contemplated that a CK1 inhibitors may be chemically substituted to optimize the activity of the modulator, e.g., to improve solubility, to improve delivery across the blood brain barrier, to improve lipophylicity, and/or to reduce cell toxicity. Chemical modifications of this sort may be achieved according to conventional methods familiar to one of skill in the art.

Similarly, it is contemplated herein that monitoring CK1 protein levels or kinase activity and/or detecting CK1 gene expression (mRNA levels) may be used as part of a clinical testing procedure, for example, to determine the efficacy of a given treatment regimen in accordance with any of the methods of the invention. For example, Alzheimer's patients undergoing conventional therapy may be evaluated and patients in whom CK1 levels, activity and/or gene expression levels are higher than desired (i.e. levels greater than levels in control patients) may be identified. Based on these data, the patient's dosage regimen may be adjusted and/or the type of drug administered may be modified. It is contemplated herein that monitoring a patient's levels of CK1 as described above may provide a quantitative assessment of a patient's physical and/or mental state.

Factors for consideration for optimizing a therapy for a patient include the particular condition being treated, the particular mammal being treated, the clinical condition of the individual patient, the site of delivery of the active compound, the particular type of the active compound, the method of administration, the scheduling of administration, and other factors known to medical practitioners. The therapeutically effective amount of an active compound to be administered will be governed by such considerations, and is the minimum amount necessary for the treatment of a CK1 related disorder, preferably Alzheimer's disease.

The pharmaceutical compositions of the present invention may be prepared using conventional diluents or excipients and techniques known in the galenic art. Thus oral dosage forms may include tablets, capsules, solutions, suspensions, spray-dried dispersions [e.g. Eudragit L100] and the like. The term "pharmaceutically acceptable carrier" as used herein is intended to include diluents such as saline and aqueous buffer solutions. The compounds of the invention may be administered in any convenient manner such as by injection (such as subcutaneous or intravenous), by oral administration, inhalation, transdermal application, intravaginal application, topical application, intranasal, sublingual or rectal administration. Depending on the route of administration, the active compound may be coated in a material to protect the compound from degradation by enzymes, acids and other natural conditions that may inactivate the compound.

The pharmaceutical compositions disclosed herein useful for treating CK1 related disorders, or disorders associated with abnormally hyperphosphorylated Tau state including Alzheimer's disease, are to be administered to a patient at therapeutically effective doses to treat symptoms of such disorders. A "therapeutically effective amount" is the amount of drug (e.g., CK1 inhibitor) sufficient to treat a CK1 related disorder or a disorder that can be benefited from the inhibition of CK1. For example, a therapeutically effective amount of a CK1 inhibitor may be an amount shown to inhibit, totally or partially, the progression of the condition or alleviate, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount may be determined by methods known to those of skill in the art.

A therapeutically effective dose refers to that amount of the compound that results in amelioration of symptoms in a patient. Toxicity and therapeutic efficacy of such compounds can be determined by standard pharmaceutical procedures in cell cultures or experimental animals.

Improvements in the physical and/or mental state of an individual suffering from Alzheimer's disease may be measured by techniques and combinations of techniques familiar to one of skill in the art, including but not limited to, Clinical Dementia Rating (CDR) assessment, the mini-mental state exam (MMSE), the mini-cog exam, as well as positron emission tomography (PET), magnetic resonance imaging (MRI) and computed tomography (CT). Further diagnostic tests may include tests of biological fluids and tissues for various biochemical markers and activities.

CK1 inhibitors may be used in the methods disclosed herein as a sole therapeutic agent, but it is contemplated herein that they may also be used in combination with or for co-administration with other active agents. For example, any one or more CK1 inhibitors may be simultaneously, sequentially, or contemporaneously administered with conventional medications proven useful for the treatment of Alzheimer's disease. These medications include cholinesterase inhibitors such as Razadyne® (formerly known as Reminyl®) (galantamine), Exelon® (rivastigmine), Aricept® (donepezil), and Cognex® (tacrine) as well as Namenda® (memantine), an N-methyl D-aspartate (NMDA) antagonist.

The inhibitory substances of the present invention can be administered as pharmaceutical compositions. Such pharmaceutical compositions for use in accordance with the present invention may be formulated in a conventional manner using one or more physiologically acceptable carriers or excipients.

Thus, the compounds and their physiologically acceptable salts and solvates may be formulated for administration by inhalation or insufflation (either through the mouth or the nose) or topical, oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially using either cell culture assays, e.g., of suitable cells, or animal models. The animal model may also be used to determine the appropriate concentration range and route of administration. A dose may be formulated in animal models to achieve a circulating plasma concentration range that includes the $IC_{50}$ (i.e., the concentration of the test compound that achieves a half-maximal inhibition of symptoms). Such information can then be used to determine useful doses and routes for administration in humans.

With regard to a therapeutically effective dose of a CK1 inhibitor, therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies are used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Dosages employed in practicing the present invention will of course vary depending, e.g. on the particular disease or condition to be treated, the particular CK1 inhibitor used, the mode of administration, and the therapy desired. CK1 inhibitors for use in the instant invention may be administered by any suitable route, including orally, parenterally, transdermally, or by inhalation, but are preferably administered orally. In general, satisfactory results, e.g. for the treatment of diseases as hereinbefore set forth, are indicated to be obtained on oral administration at dosages of the order from about 0.01 to 10.0 mg/kg (all weights are given as the equivalent of CK1 inhibitor in free form, although the inhibitor may be provided in free or pharmaceutically acceptable salt form). In larger mammals, for example humans, an indicated daily dosage for oral administration will accordingly be in the range of from about 0.75 to 750 mg, e.g., 50-500 mg, conveniently administered once, or in divided doses 2 to 4 times daily, or in sustained release form. Unit dosage forms for oral administration thus for example may comprise from about 0.2 to 250 mg, e.g. from about 0.2 or 2.0 to 50, 75, 100 or 200 mg of CK1 inhibitor, together with a pharmaceutically acceptable diluent or carrier therefor.

It is intended that the compounds of the invention encompass their stable isotopes. For example, the hydrogen atom at a certain position on the compounds of the invention may be replaced with deuterium. It is expected that the activity of compounds comprising such isotopes would be retained and/or it may have altered pharmacokinetic or pharmacodynamic properties. In addition to therapeutic use, compounds comprising such isotopes and having altered pharmacokinetic or pharmacodynamic properties would also have utility for measuring pharmacokinetics of the non-isotopic analogs.

It is also intended that the compounds of the invention encompass compounds having chemically bound radionuclide such as those selected from Carbon-11 (referred to as $^{11}$C or C$^{11}$), Fluorine-18 (referred to as $^{18}$F or F$^{18}$), Technetium-99m (referred to as $^{99m}$Tc or Tc$^{99m}$), Indium-111 (referred to as $^{111}$In or In$^{111}$) and Iodine-123 (referred to as $^{123}$I or I$^{123}$), preferably $^{11}$C or $^{18}$F for use as, e.g., PET or SPECT tracer compounds. The radio-labelled compounds may be prepared, for example as follows:

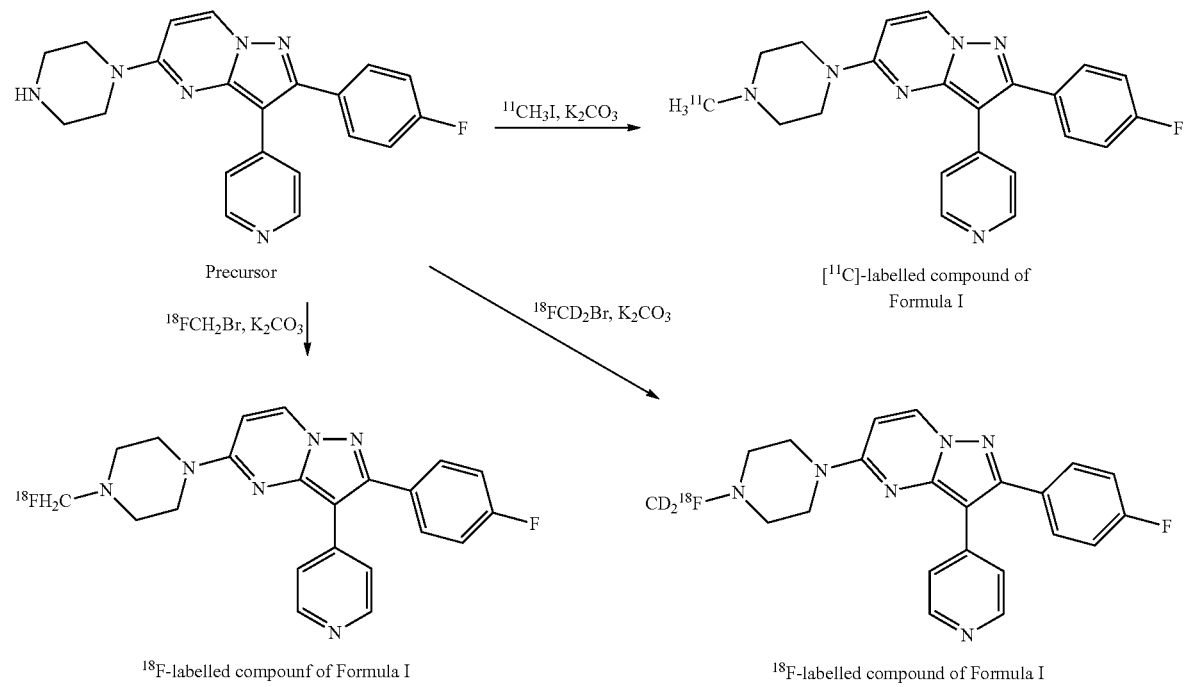

The following examples further illustrate the present invention and are not intended to limit the invention.

EXAMPLES

The compounds of the invention, in free or salt form may be made using the methods as described and exemplified herein and by methods similar thereto and by methods known in the chemical art. Such methods include, but are not limited to, those described below. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, the reaction may require to be run at elevated temperature or for a longer or shorter period of time. It is understood by one skilled in the art of organic synthesis that functionality present on various portions of the molecule must be compatible with the reagents and reactions proposed. If not commercially available, starting materials for these processes may be made by procedures, which are selected from the chemical art using techniques which are similar or analogous to the synthesis of known compounds. All references cited herein are hereby incorporated by reference in their entirety.

The synthetic methods for the compounds of the invention are illustrated below either in the generic synthetic scheme and/or in the specific Examples, which methods are claimed individually and/or collectively. The significances for the substituents are as set forth above unless otherwise indicated.

Example 1

2-(4-Fluorophenyl)-5-(4-methylpiperazin-1-yl)-3-(pyridin-4-yl)pyrazolo[1,5-a]pyrimidine

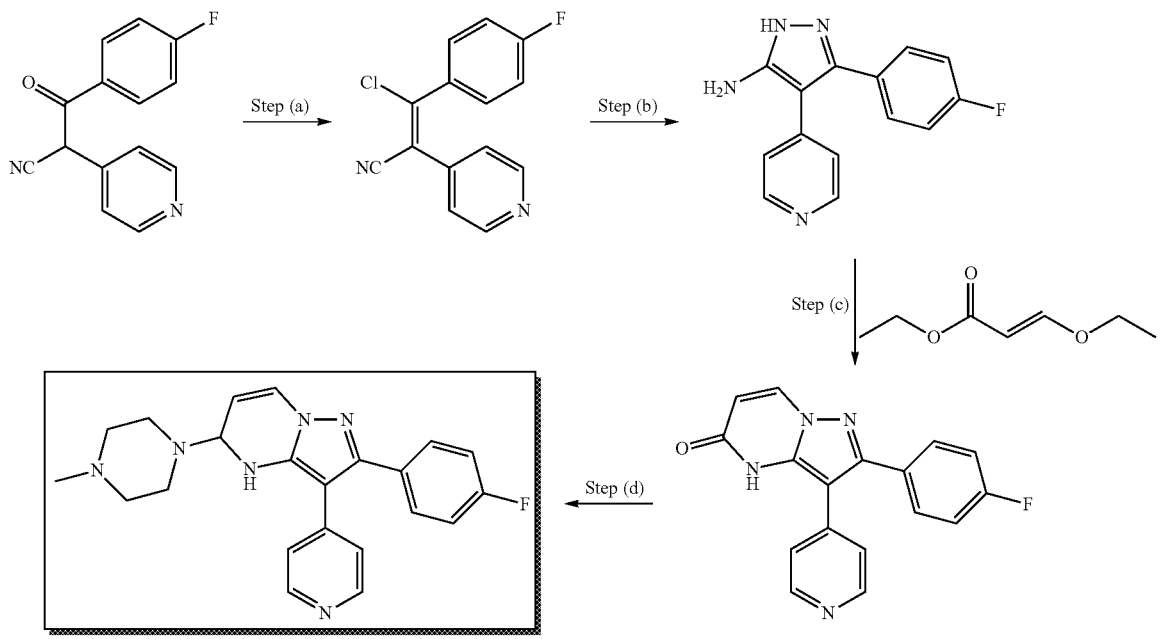

Step (a)—(Z)-3-Chloro-3-(4-fluorophenyl)-2-(pyridin-4-yl)acrylonitrile: 3-(4-Fluorophenyl)-3-oxo-2-(pyridine-4-yl)propanenitrile (330 mg, 1.37 mmol) is added to $POCl_3$ (5 mL) at room temperature. The mixture is heated at 120° C. for an hour, and then cooled to room temperature. After excessive $POCl_3$ is removed under reduced pressure, the residue is treated with dichloromethane and ice, and then basified with 10N NaOH. The organic layer is separated, dried over sodium sulfate and concentrated. The obtained crude product is purified by silica-gel flash chromatography to give 200 mg of (Z)-3-chloro-3-(4-fluorophenyl)-2-(pyridin-4-yl)acrylonitrile as a brown oil (57% yield). MS (ESI) m/z 259.1 [M+H]$^+$.

Step (b)—3-(4-Fluorophenyl)-4-(pyridin-4-yl)-1H-pyrazol-5-amine: To a solution of (Z)-3-chloro-3-(4-fluorophenyl)-2-(pyridin-4-yl)acrylonitrile (190 mg, 0.74 mmol) in ethanol (5 mL) is added hydrazine hydrate (0.075 mL, 1.5 mmol). The mixture is heated at 100° C. overnight, and then cooled to room temperature. Solvent is removed under reduced pressure to give crude 3-(4-fluorophenyl)-4-(pyridin-4-yl)-1H-pyrazol-5-amine as a redish solid, which is used directly in next step without further purification. MS (ESI) m/z 255.1 [M+H]$^+$.

Step (c)—2-(4-Fluorophenyl)-3-(pyridin-4-yl)pyrazolo[1,5-a]pyrimidin-5(4H)-one: To a solution of 3-(4-fluorophenyl)-4-(pyridin-4-yl)-1H-pyrazol-5-amine (61 mg, 0.24 mmol) in DMF (4 mL) is added (E)-ethyl 3-ethoxyacrylate (0.053 mL, 0.37 mmol), followed by $K_2CO_3$ (47 mg, 0.24 mmol). The mixture is heated at 110° C. for 9 h, and then cooled to room temperature. After filtration, the filtrate is concentrated under reduced pressure. The residue is purified by column chromatography to yield 50 mg of 2-(4-fluorophenyl)-3-(pyridin-4-yl)pyrazolo[1,5-a]pyrimidin-5(4H)-one as a brown solid (68% yield). MS (ESI) m/z 307.1 [M+H]$^+$.

Step (d)—2-(4-Fluorophenyl)-5-(4-methylpiperazin-1-yl)-3-(pyridin-4-yl)pyrazolo[1,5-a]pyrimidine: 2-(4-Fluorophenyl)-3-(pyridin-4-yl)pyrazolo[1,5-a]pyrimidin-5(4H)-one (15 mg, 0.05 mmol) and $K_2CO_3$ (20.6 mg, 0.15 mmol) are suspended in DMF (1.0 mL), and then N-phenyl-bis(trifluoromethanesulfonimide) (35.8 mg, 0.1 mmol) is added. The reaction mixture is stirred at room temperature overnight. 1-methylpiperazine 0.5 mL is added and the mixture is stirred for additional 2 h. After the solvent is removed, the obtained residue is purified by preparative TLC to give 5 mg of 2-(4-fluorophenyl)-5-(4-methylpiperazin-1-yl)-3-(pyridin-4-yl)pyrazolo[1,5-a]pyrimidine as a brown solid (26% yield). MS (ESI) m/z 389.2 [M+H]$^+$.

Example 2

(E)-N-((1H-benzo[d]imidazol-2-ylamino)(amino)methylene)-2-(pyridin-3-yl)acetamide

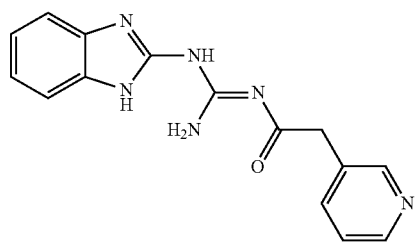 [SMILES: N/C(=N\C(=O)Cc1cccnc1)Nc1nc2ccccc2[nH]1]

Step (a) 1-(1H-benzo[d]imidazol-2-yl)guanidine: O-phenylenediamine (2.2 g, 20 mmol) and dicyandiamide (1.7 g, 20 mmol) are added into 4 mL of conc.HCl. The mixture is heated to reflux with vigorous stirring. After an hour of reflux, the mixture is cooled to room temperature, and then 10N NaOH (5 mL) is added carefully with temperature controlled below 30° C. The resulting precipitate is filtered and dried under vacuum to give 2.5 g of crude product as a tan powder (70% yield), which is used in next step without further purification. MS (ESI) m/z 176.1 [M+H]$^+$.

Step (b) (E)-N-((1H-benzo[d]imidazol-2-ylamino)(amino)methylene)-2-(pyridin-3-yl)acetamide: 1-(1H-Benzo[d]imidazol-2-yl)guanidine (175 mg, 1.0 mmol), 2-(pyridin-3-yl)acetic acid (165 mg, 1.2 mmol), diisopropylethylamine (222 μL, 1.3 mmol), and O-(Benzotriazol-1-yl)-N,N,N',N'-tetramethyluronium tetrafluoroborate (TBTU, 385 mg, 1.2 mmol) are added in sequence into 2 mL of DMF. The mixture is stirred at room temperature overnight. The mixture is treated with water (1 mL), and then extracted with dichloromethane three times (3×3 mL). The combined organic phase is dried over sodium sulfate, and then concentrated under reduced pressure. The obtained residue is purified by preparative TLC, followed by HPLC purification to give the final product as a pale yellow powder. MS (ESI) m/z 295.1 [M+H]$^+$.

Example 3

(E)-N-((1H-benzo[d]imidazol-2-ylamino)(amino)methylene)-2-(naphthalen-1-yl)acetamide

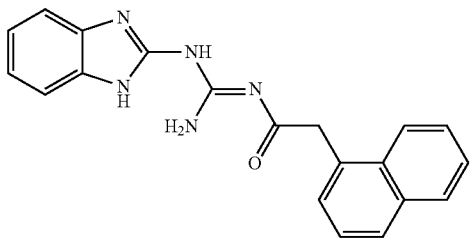 [SMILES: N/C(=N\C(=O)Cc1cccc2ccccc12)Nc1nc2ccccc2[nH]1]

The title compound is prepared using a method analogous to that for Example 2 except that 2-(naphthalen-1-yl)acetic acid is added in step (b) instead of 2-(pyridin-3-yl)acetic acid. MS (ESI) m/z 344.1 [M+H]$^+$.

Example 4

(E)-N-((1H-benzo[d]imidazol-2-ylamino)(amino)methylene)-2-(pyridin-4-yl)acetamide

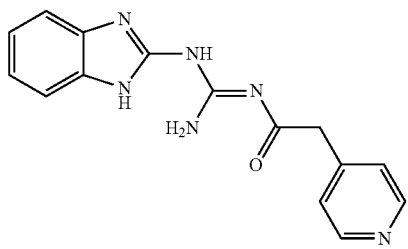 [SMILES: N/C(=N\C(=O)Cc1ccncc1)Nc1nc2ccccc2[nH]1]

The title compound is prepared using a method analogous to that for Example 2 except that 2-(pyridin-4-yl)acetic acid is added in step (b) instead of 2-(pyridin-3-yl)acetic acid. MS (ESI) m/z 295.1 [M+H]$^+$.

Example 5

2-(4-acetamidophenyl)-N-(6-tert-butylbenzo[d]thiazol-2-yl)acetamide

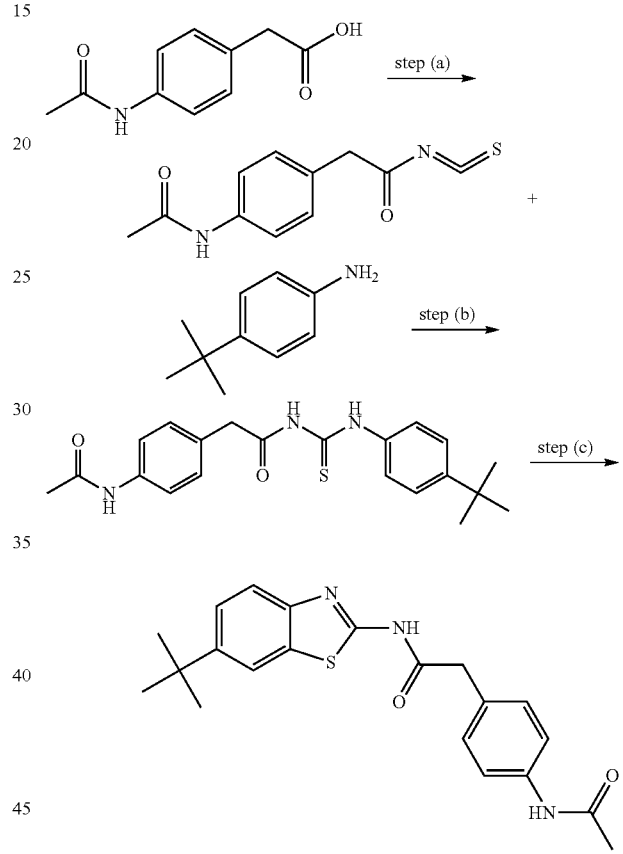

Step (a) 2-(4-Acetamidophenyl)acetyl isothiocyanate. 2-(4-Acetamidophenyl)acetic acid (1.34 g, 6.9 mmol) is dissolved in 20 mL CH$_3$CN and triphosgene (0.69 g, 0.33 mmol) is added under stirring. 6 drops of DMF is added slowly and the mixture is then heated to 60° C. for 1.0 h. After cooling to room temperature, Ammonium isocyanate (1.05 g, 13.8 mmol) is added, and the mixture is stirred over night at room temperature. The crude 2-(4-acetamidophenyl)acetyl isothiocyanate is used directly without any further purification.

Step (b) 2-(4-acetamidophenyl)-N-(4-tert-butylphenylcarbamothioyl)-acetamide. 4-Tert-butylbenzenamine (149 mg, 1.0 mmol) is dissolved in 1.0 mL CH$_3$CN and crude 2-(4-acetamidophenyl)acetyl isothiocyanate, which is prepared as above (3 mL, 1.0 mmol) is dropped in and the yellow mixture is stirred at room temperature. 1.0 h later, the mixture is concentrated and residue is purified by silica gel column chromatography (ethyl acetate: hexanes=1:1) to give product as yellow solid (100 mg, 26% yield). MS (ESI) m/z 384.2 [M+H]+.

Step (c) 2-(4-acetamidophenyl)-N-(6-tert-butylbenzo[d]thiazol-2-yl)acetamide. 2-(4-Acetamidophenyl)-N-(4-tert-butylphenylcarbamothioyl)acetamide (38 mg, 0.1 mmol) is dissolved into 1.0 mL CH$_3$SO$_3$H and 0.2 mL glacial CH$_3$COOH at room temperature. Under stirring, 3 drops of bromine is added carefully. The red mixture is stirred vigorously for 1.0 h at room temperature and then poured onto ice to quench the reaction. The mixture is extracted with dichloromethane and the organic solution is dried and concentrated. The obtained residue is purified by preparative TLC (ethyl acetate:hexanes=2:1), followed by HPLC purification to give final product as light yellow powder (14 mg, 36% yield). MS (ESI) m/z 382.1 [M+H]+.

Example 6

2-(4-bromophenyl)-N-(6-methylbenzo[d]thiazol-2-yl)acetamide

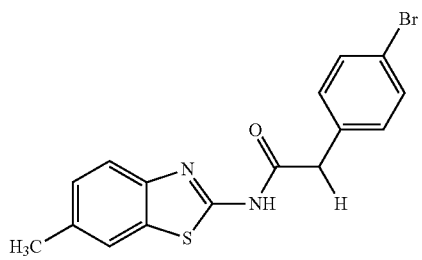 [SMILES: Cc1ccc2nc(NC(=O)Cc3ccc(Br)cc3)sc2c1]

The title compound is prepared using a method analogous to that for Example 5 except that 2-(4-bromophenyl)acetic acid is used in step (a) instead of 2-(4-acetamidophenyl)acetic acid, and p-toluidine is used instead of 4-tert-butylbenzenamine in step (b). MS (ESI) m/z 361.1 [M+H]+.

Example 7

2-(4-hydroxyphenyl)-N-(6-methylbenzo[d]thiazol-2-yl)acetamide

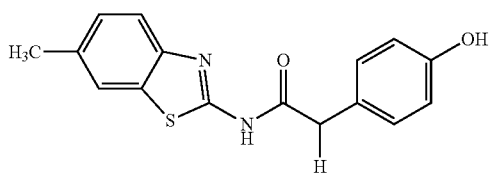 [SMILES: Cc1ccc2nc(NC(=O)Cc3ccc(O)cc3)sc2c1]

The title compound is prepared using a method analogous to that for Example 5 except that 2-(4-hydroxyphenyl)acetic acid is used in step (a) instead of 2-(4-acetamidophenyl)acetic acid, and p-toluidine instead of 4-tert-butylbenzenamine in step (b). MS (ESI) m/z 299.1 [M+H]+.

Example 8

2-(4-(dimethylamino)phenyl)-N-(6-methylbenzo[d]thiazol-2-yl)acetamide

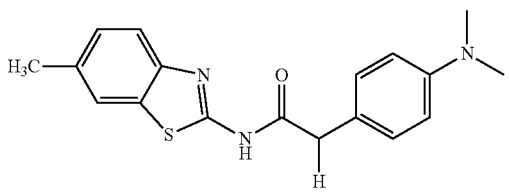

The title compound is prepared using a method analogous to that for Example 5 except that 2-(4-(dimethylamino)phenyl)acetic acid is used in step (a) instead of 2-(4-acetamidophenyl)acetic acid, and p-toluidine instead of 4-tert-butylbenzenamine in step (b). MS (ESI) m/z 326.1 [M+H]+.

Example 9

2-(4-acetamidophenyl)-N-(6-ethylbenzo[d]thiazol-2-yl)acetamide

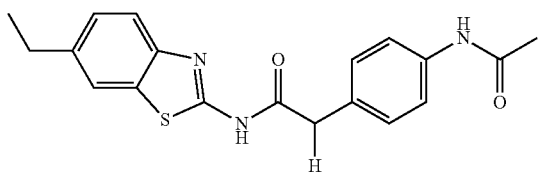 [SMILES: CCc1ccc2nc(NC(=O)Cc3ccc(NC(C)=O)cc3)sc2c1]

The title compound is prepared using a method analogous to that for Example 5 except that 4-ethylbenzenamine is used instead of 4-tert-butylbenzenamine in step (b). MS (ESI) m/z 354.1 [M+H]+.

Example 10

2-(4-acetamidophenyl)-N-(6-acetylbenzo[d]thiazol-2-yl)acetamide

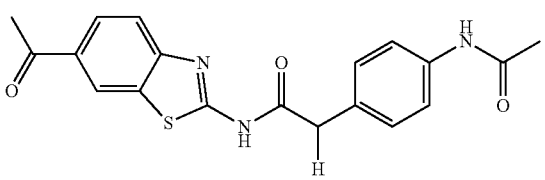 [SMILES: CC(=O)Nc1ccc(CC(=O)Nc2nc3ccc(C(C)=O)cc3s2)cc1]

The title compound is prepared using a method analogous to that for Example 5 except that 1-(4-aminophenyl)ethanone is used instead of 4-tert-butylbenzenamine in step (b). MS (ESI) m/z 368.1 [M+H]+.

Example 11

N-(7-ethynylbenzo[d]thiazol-2-yl)-2-phenylacetamide

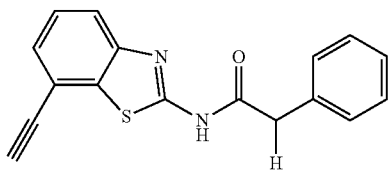 [SMILES: C#Cc1cccc2nc(NC(=O)Cc3ccccc3)sc12]

The title compound is prepared using a method analogous to that for Example 5 except that starts with 2-phenylacetic acid in step (a) instead of 2-(4-acetamidophenyl)acetic acid, and 3-ethynylbenzenamine instead of 4-tert-butylbenzenamine in step (b). MS (ESI) m/z 293.1 [M+H]$^+$.

Example 12

(S)-2-hydroxy-N-(6-methylbenzo[d]thiazol-2-yl)-2-phenylacetamide

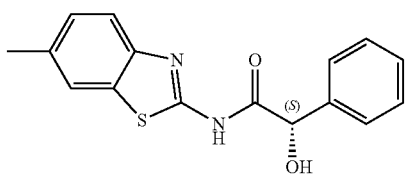

The title compound is prepared using a method analogous to that for Example 5 except that starts with (S)-2-hydroxy-2-phenylacetic acid in step (a) instead of 2-(4-acetamidophenyl)acetic acid, and p-toluidine instead of 4-tert-butylbenzenamine in step (b). MS (ESI) m/z 299.1 [M+H]$^+$.

Example 13

(R)-2-amino-N-(6-methylbenzo[d]thiazol-2-yl)-2-phenylacetamide

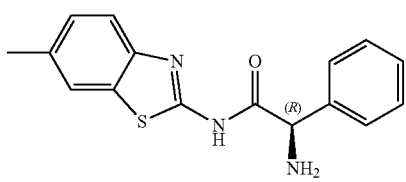

The title compound is prepared using a method analogous to that for Example 5 except that starts with (R)-2-amino-2-phenylacetic acid in step (a) instead of 2-(4-acetamidophenyl)acetic acid, and p-toluidine instead of 4-tert-butylbenzenamine in step (b). MS (ESI) m/z 298.1 [M+H]$^+$.

Example 14

The kinase inhibition assays are conducted by using γ-$^{33}$P-ATP as the radioligand. The targeted kinase is the human CK1δ. The Km for ATP and CK1δ is determined as 70-77 μM at Millipore. The concentration of ATP used in the assays is within 15 μM of the apparent Km for ATP. All experiments are performed as duplicates. Staurosporine is used as the internal reference inhibitor and its IC50 falls between 3.798 μM to 34.18 μM. The exemplified compounds are tested at 10 μM during the initial screening and 1 μM during the confirmation assays. The IC50 value may be converted to Ki values by using methods known to one skilled in the art, such as the Cheng-Prusoff Equation disclosed in Hsien C. Cheng, *Journal of Pharmacological and Toxicological Methods* (2002) 46:61-71, the contents of which are incorporated by reference in their entirety.

Example 15

In a final reaction volume of 25 μl, CK1δ (5-10 mU) is incubated with 8 mM MOPS pH 7.0, 0.2 mM EDTA, 200 μM KRRRALS(p)VASLPGL, 10 mM MgAcetate and [γ-33P-ATP] (specific activity approx. 500 cpm/pmol, concentration as required). The reaction is initiated by the addition of the ATP/Mg mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

The compounds exemplified in formulae 1.3, 2.16 and 3.28 are tested and shown to generally inhibit CK1δ and/or CK1ε with a IC$_{50}$ of less than 15 μM, most inhibit CK1δ and/or CK1ε with a IC$_{50}$ of less than 2 μM, many less than 500 nM, as described or similarly described in Example 14 or inhibit greater than 70% of CK1δ and/or CK1ε at 10 μM as described or similarly described in Example 15.

What is claimed is:

1. A compound of Formula I:

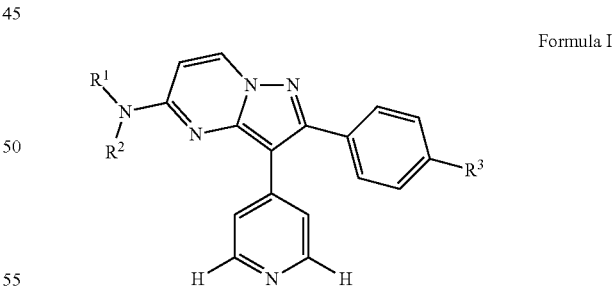

Formula I in free or salt form, wherein:
 (i) R$^3$ is halo; and
 (ii) R$^1$ and R$^2$ together form a piperazine ring wherein said piperazine is optionally substituted with a C$_{1-6}$ alkyl.

2. The compound according to claim 1, wherein the piperazine ring is substituted with a C$_{1-6}$ alkyl; and R$^3$ is fluoro, in free or salt form.

3. The compound according to claim 1, wherein said compound is:

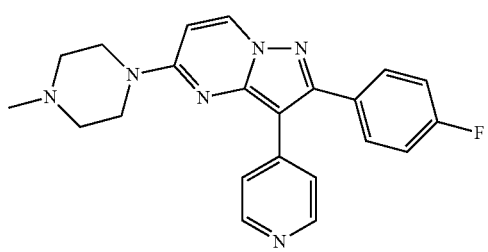 [SMILES: CN1CCN(c2ccn3nc(-c4ccc(F)cc4)c(-c4ccncc4)c3n2)CC1]

in free or salt form.

4. The compound according to claim 1, in free or pharmaceutically acceptable salt form, which is radio-labelled with a chemically bound radionuclide.

5. The compound according to claim 4, wherein the radionuclide is selected from, Technetium-99m, Indium-111 and Iodine-123.

6. The compound according to claim 1 selected from any of the following:

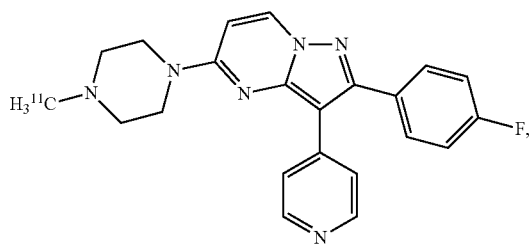

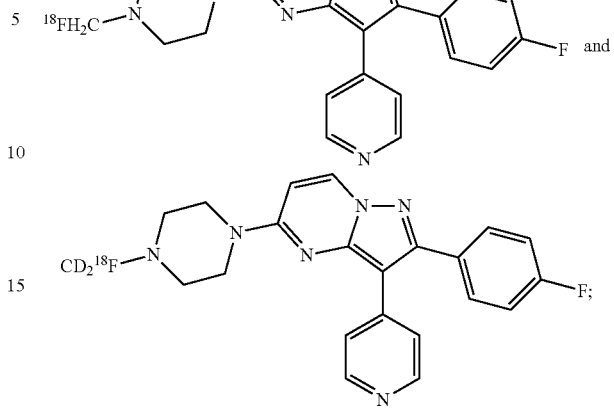

in free or pharmaceutically acceptable salt form.

7. A pharmaceutical composition comprising the compound according to claim 1, in free or pharmaceutically acceptable salt form, and a pharmaceutically acceptable diluent or carrier.

8. A method for inhibiting CK1 activity, particularly CK1δ and CK1ε activity, comprising contacting CK1, particularly CK1δ and CK1ε, with the compound according to claim 1, in free or salt form.

* * * * *